United States Patent [19]
Harrison

[11] Patent Number: 5,530,422
[45] Date of Patent: Jun. 25, 1996

[54] DIFFERENTIALLY DRIVEN TRANSMISSION LINE FOR HIGH DATA RATE COMMUNICATION IN A COMPUTERIZED TOMOGRAPHY SYSTEM

[75] Inventor: Daniel D. Harrison, Delanson, N.Y.

[73] Assignee: General Electric Company, Schenectady, N.Y.

[21] Appl. No.: 307,118

[22] Filed: Sep. 16, 1994

[51] Int. Cl.⁶ ........................................................ A61B 6/00
[52] U.S. Cl. ................................. 340/500; 378/4; 378/15
[58] Field of Search .................... 340/500, 540, 340/539, 671; 455/66, 67.1; 333/109, 116, 243; 343/700 MS; 378/4, 15, 98; 364/413.14, 413.15; 250/370.08, 370.09

[56] References Cited

U.S. PATENT DOCUMENTS

| | | | |
|---|---|---|---|
| 4,651,338 | 3/1987 | Hahn | 378/15 X |
| 5,140,696 | 8/1992 | Fox | 378/15 X |
| 5,157,393 | 10/1992 | Fox et al. | 378/15 X |
| 5,208,581 | 5/1993 | Collins | 378/4 X |
| 5,229,871 | 7/1993 | Czarnek et al. | 359/15 |
| 5,287,117 | 2/1994 | Posluszny | 378/15 X |

*Primary Examiner*—Thomas Mullen
*Attorney, Agent, or Firm*—Marvin Snyder

[57] ABSTRACT

A computerized tomography (CT) system includes a stationary frame and an annular rotating frame. The CT system further includes a differentially driven transmission line attached to the rotating frame and positioned around the rotating frame. The differentially driven transmission line is made up of individual segments each having a respective first end and a respective second end and having a respective electrical length chosen so that a modulated signal simultaneously applied at each respective first end has a predetermined time-delay upon arrival at each respective second end. The individual segments are arranged so that respective first ends of any two consecutive segments are substantially adjacent to one another and respective second ends of any two consecutive segments are substantially adjacent to one another to avoid time-delay discontinuity in the modulated signal propagating therethrough. A transmission line shield is affixed to the transmission line and defines a passage for shielding the transmission line from electromagnetic radiation. A differential coupler is attached to the stationary frame and is positioned in the passage sufficiently near the transmission line for establishing radio coupling therebetween so as to receive the modulated signal being applied to the respective individual segments. A coupler shield is optionally provided for shielding the coupler from electromagnetic radiation.

46 Claims, 5 Drawing Sheets

DIFFERENTIALLY DRIVEN TRANSMISSION LINE FOR HIGH DATA RATE COMMUNICATION IN A COMPUTERIZED TOMOGRAPHY SYSTEM

RELATED APPLICATIONS

This application is related to patent application Ser. No. 08/307,120 by D. D. Harrison et al, entitled "Apparatus and Method For High Data Rate in a Computerized Tomography System", filed on Sep. 16,1994; patent application Ser. No. 08/307,130 by D. D. Harrison, entitled "Radiation Shielded Apparatus For High Data Rate Communication in a Computerized Tomography System" filed on Sep. 16,1994; and patent application Ser. No. 08/307,119 by D. D. Harrison, entitled "A Transmission Line With A Grounding Brush For High Data Rate Communication In A Computerized Tomography System" filed on Sep. 16,1994. Each of the above listed related applications is assigned to the assignee of the present invention and is herein incorporated by reference.

BACKGROUND OF THE INVENTION

The field of the present invention is generally related to computerized tomography (CT) and, particularly, to a differentially driven transmission line for high data rate communication in a CT system.

CT systems typically employ a rotating frame or gantry to obtain multiple x-ray images, or views, at different rotational angles. Each set of images is referred to in the art as a "slice". A patient or inanimate object is generally positioned in a central opening of the rotating frame on a table which is movable axially, thus enabling respective slices to be obtained at multiple axial positions as well. Each of the slices obtained is then processed in a computer according to predetermined algorithms to produce enhanced images for diagnostic or inspection purposes.

The rotating frame includes an x-ray source, a detector array and electronics necessary to generate image data for each view. A set of stationary electronics is employed for processing raw image data into the enhanced form. Thus, it is necessary to provide for communication of the image data between the rotating frame and a stationary frame of the CT system.

The data rate for communication between the stationary and rotating frames is an important factor because it is desirable to obtain the desired views as fast as possible to reduce patient discomfort and/or to maximize equipment utilization. In current CT systems, a single view typically comprises about 800 detector channels with a 16 bit representation for each individual detector channel output (i.e., 12.8 Kbits per view) and is typically repeated 1,000 times per second, yielding a net data rate requirement of approximately 13 Megabits per second (Mbit/sec) for image data alone. Future CT systems capable of simultaneously constructing multiple image slices by employing four, eight, or sixteen times as many detector channels will increase the data rate requirement to beyond 150 Mbit/sec for image data alone.

Prior CT systems have employed brushes and slip rings for electrically linking the rotating frame to the stationary frame. However, in general, CT systems utilizing brushes and slip rings for communications have generally suffered from significant limitations in the data rates which can be achieved. This is due to the substantial time required to propagate the signals around the circular slip rings. At the desired data rates, the electrical path length around the rings is an appreciable fraction of a bit period, so that electromagnetic waves propagating around the rings in opposite directions may arrive at a reception point at substantially different times in a bit period, causing garbled reception.

U.S. Pat. No. 5,208,581 issued to A. K. Collins, assigned to the assignee of the present invention and herein incorporated by reference, is another type of gantry in which brushes and slip tings are employed for communication. Although the design of Collins provides relatively high speed communication between the stationary and rotating frames, the fact remains that the use of contacting brushes and rings inherently carries certain disadvantages. For example, the mechanical contact between the brushes and rings causes wear out which requires such brushes and tings to be periodically replaced in order to maintain reliable communication. Furthermore, the slip-ring design of Collins does not support the higher data rates needed for multiple-slice CT systems.

Other CT systems have employed an optical data link for communication between the stationary and rotating frames. Although an optical data link design avoids typical drawbacks of slip rings and brushes, such optical design requires optics which must be fabricated under tight specifications and which in operation require substantial spatial alignment in order to achieve reliable optical coupling along the relatively long circumference of the rotating frame. This leads to high costs and, thus, it is desirable to provide in a CT system an improved communication link which at a low cost provides reliable high data ram communication between the stationary and rotating frames of the CT system.

It is further desirable to provide a communication link between the stationary frame and the rotating frame which is robust with respect to electromagnetic radiation interference such as is typically produced in a hospital environment by cellular telephones, defibrillating devices, surgical saws and even electrical noise produced by any given CT system. Furthermore, it is also desirable to reduce the level of electromagnetic energy which is radiated from such communication link in order to comply with governmental regulations such as regulations imposed by the Federal Communications Commission and/or foreign governments. As disclosed in U.S. patent application Ser. No. 08/307,120, a transmission line and a coupler or probe provide means for implementing such high data rate communication link. As further disclosed in U.S. patent application Ser. No. 08/307, 130, a U-shaped structure is effectively employed for substantially reducing electromagnetic radiation from the transmission line while providing a passage which allows for the coupler to readily access the transmission line. Although such U-shaped structure effectively shields the transmission line, it is desirable to reduce electromagnetic radiation which escapes or leaks around the coupler. It is also desirable to reduce sensitivity of the coupler to eternally produced electromagnetic energy which can interfere with coupler operation.

SUMMARY OF THE INVENTION

Generally speaking, the present invention fulfills the foregoing needs by providing in a computerized tomography (CT) system having a stationary frame and a generally annular rotating frame, an apparatus comprising a differentially driven transmission line attached to the rotating frame and positioned substantially around the rotating frame. The differentially driven transmission line comprises individual segments each having a respective first end and a respective second end and having a respective electrical length chosen so that a modulated signal simultaneously applied at each respective first end has a predetermined time-delay upon arrival at each respective second end. The individual segments are arranged so that respective first ends of any two consecutive segments are substantially adjacent to one another and respective second ends of any two consecutive segments are substantially adjacent to one another to avoid time delay discontinuity in the modulated signal propagating therethrough. The apparatus further comprises transmission line shield means such as a U-shaped structure affixed to the transmission line for shielding the transmission line from electromagnetic radiation. The shield means defines a passage around the rotating frame. A differential coupler is attached to the stationary frame and is positioned in the passage sufficiently near the transmission line for establishing radio coupling therebetween so as to receive the modulated signal being applied to the respective individual segments. A coupler shield can also be provided for shielding the coupler from electromagnetic radiation.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description in conjunction with the accompanying drawings in which like numbers represent like parts throughout the drawings, and in which:

DETAILED DESCRIPTION OF THE INVENTION

Figure 1:
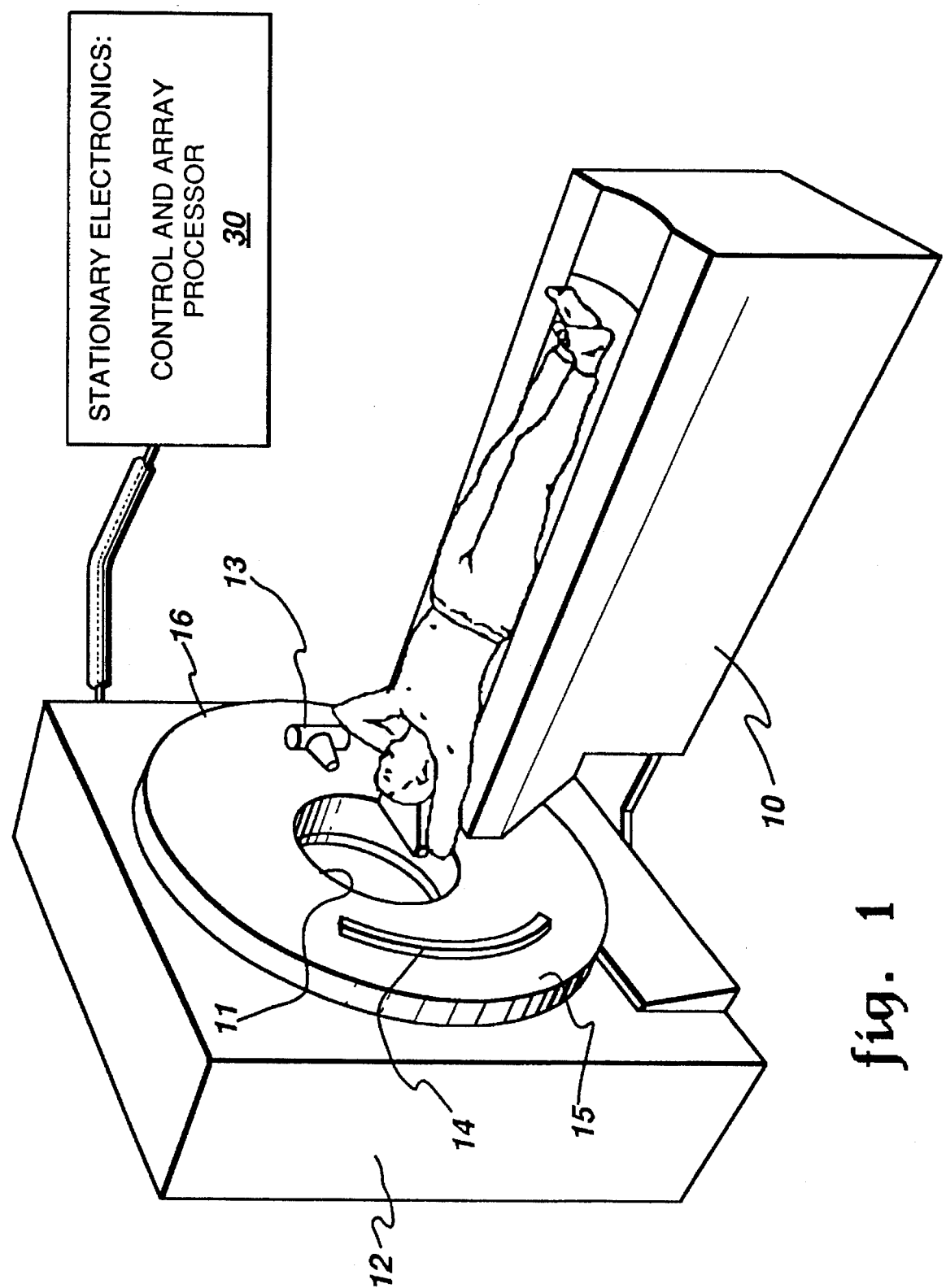
FIG. 1 is a perspective view of a CT system which employs the present invention.

As shown in FIG. 1, a CT system used to produce images of at least a region of interest of the human anatomy has a patient table 10 which can be positioned within the aperture 11 of a generally annular rotating frame or gantry 15 having a predetermined circumference, e.g., outer circumference 16. A stationary frame 12 is conveniently employed to support rotating frame 15. A source of imaging energy 13 which preferably produces highly collimated x-rays is mounted on the rotating frame to one side of its aperture 11, and a detector array 14 is mounted to the other side of the aperture. The rotating frame, together with x-ray source 13 and detector array 14, is revolved about the aperture during a scan of the patient to obtain x-ray attenuation measurements from many different angles through a range of at least 180° of revolution. Detector array 14 may comprise multiple rows each having about 800 detector channels along its length. The individual outputs of each channel in detector array 14 is connected to a data acquisition system, DAS (not shown). When sampled, each channel output is converted by the DAS to, for example, a 16 bit digital value representing X-ray intensity.

The rotating frame further includes additional onboard electronics (not shown) which rotates along with rotating frame 15. The onboard electronics is essentially a slave to stationary electronics systems 30 which is located off rotating frame 15. Stationary electronics systems 30 is a computer-based system for issuing commands to the onboard electronics on rotating frame 15 and for receiving the resulting image data, via suitable electrical leads from stationary frame 12, to perform processing of the received image data.

The present invention is directed to apparatus for high data rate communication between the rotating frame and the stationary frame through the use of a differentially driven transmission line and a differential coupler which advantageously avoid the use of slip rings and brushes and which allow for continuous rotation of rotating frame 15. As discussed above, multiple-slice CT systems require high data rate communication. The present invention advantageously allows for such high data rate communication, (e.g., exceeding 150 Mbits/sec.) without the use of brushes and slip rings or without the use of costly optical devices. Further, the present invention allows for reliable and cost effective high data rate communication notwithstanding the relatively long circumference (approximately 13 ft) of the rotating frame.

In the discussion which follows, it is assumed that all of the communication between rotating frame 15 and stationary frame 12 has been serialized, i.e., converted from parallel to serial data for transmission and vice versa on reception, employing well known multiplexing techniques. This is done so that only a single bit stream need be transmitted, although it should be apparent to those skilled in the art that multiple parallel paths according to the present invention could be employed. In each case, multilevel or multiphase encoding techniques can be employed to further increase the maximum data rate available.

Figure 2:
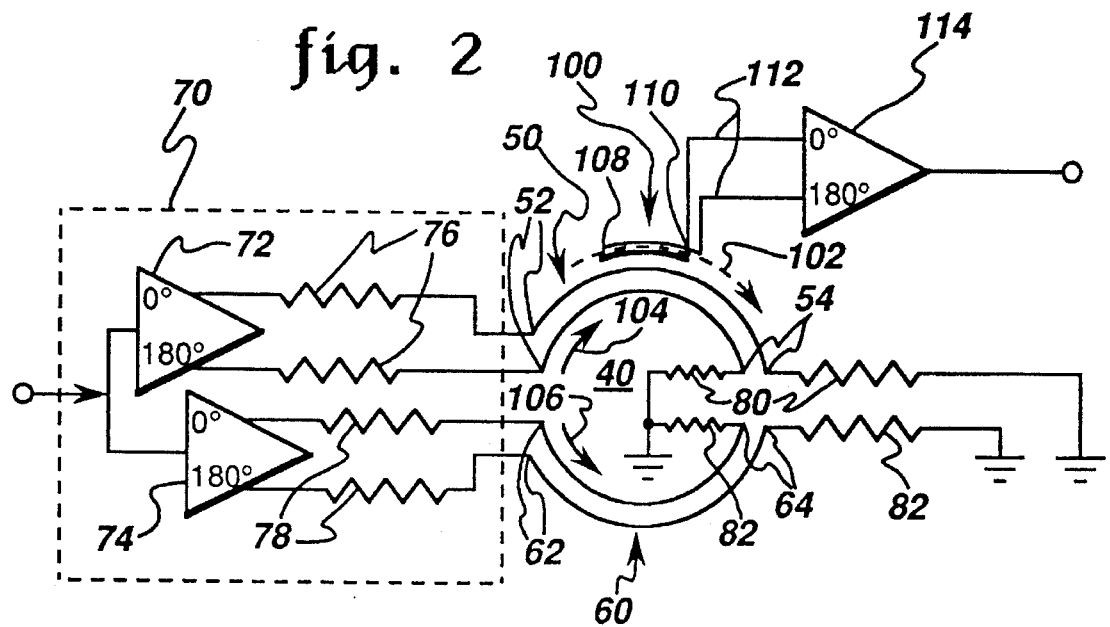
FIG. 2 is an exemplary schematic representation of an apparatus employing a differentially driven transmission line and a differential coupler in accordance with the present invention.
Figure 3:
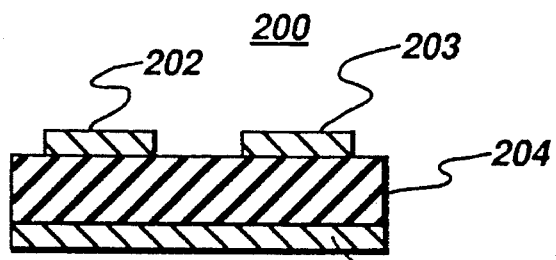
FIG. 3 is a cross section of a microstrip which can be utilized for the differentially driven transmission line and/or differential coupler in respective exemplary embodiments for the apparatus of FIG. 2.

As shown in FIG. 2, a differentially driven transmission line 40 is attached to rotating frame 15 (FIG. 1) and is positioned substantially around the rotating frame, for example, around the circumference of the rotating frame. Similarly, the transmission line can be conveniently affixed to the annulus of the rotating frame, i.e., the surface bounded by the concentric circles in the rotating frame; for example, the concentric circle which defines aperture 11 and the larger concentric circle which has circumference 16. Further, it will be appreciated that the present invention need not be limited to circular geometric arrangements since geometric arrangements other than circular can equally benefit from the present invention. Transmission line 40 comprises respective individual segments 50 and 60 each having a respective first end 52 and 62 and a respective second end 54 and 64. In FIG. 2, each respective individual segment is represented by twin lines since, as best seen in FIG. 3, each of the individual segments includes first and second signal conductors carrying respective signals being substantially 180° out-of-phase with respect to one another, that is, each transmission line segment is differentially driven. Preferably, each individual segment 50 and 60 has a respective electrical length chosen so that a modulated signal applied at each respective first end 52 and 62 has a predetermined time-delay upon arrival at each respective second end 54 and 64. It will be appreciated that if the respective electrical lengths for segments 50 and 60 are substantially similar to one another, the above-described segment arrangement results in the modulated signal arriving at each respective second end with a substantially similar time delay relative to one another.

The modulated signal, which can be conveniently supplied by the onboard electronics on rotating frame 15 employing any of a number of readily available modulation techniques such as frequency-shift keying and the like, can be readily split and phase shifted by a suitable driving circuit 70 comprising amplifiers 72 and 74 and optional matching resistors 76 and 78 having a predetermined resistance value selected to match the impedance characteristics of the respective transmission line segments. As shown in FIG. 2, amplifiers 72 and 74 can provide respective output signal being substantially 180° out-of-phase with respect to one another so that, as suggested above, each segment receives respective modulated signals which are substantially 180° out-of-phase with respect to one another. Similarly, each respective second end 54 and 64 is respectively connected to termination resistors 80 and 82 having a predetermined resistance value chosen to minimize reflection of energy in individual transmission line segments 50 and 60. Other arrangements may be employed which although having differences in time delay between individual segments, such time-delay differences can be tolerated depending on the specific application. For example, amplifier 74 and matching resistors 78 could be respectively connected to each second end 64 in lieu of each first end 62 and termination resistors 82 respectively connected to each first end 62 in lieu of each second end 64. In this case although a predetermined time delay would exist between the individual segments, such time delay could be acceptable in certain applications. Further, although driving circuit 70 is shown as comprising a pair of amplifiers, it will be apparent that a suitable single amplifier could be employed equally effective for driving individual segments 50 and 60. For example, one respective first end of segments 50 and 60 could be readily connected in parallel to receive the in-phase output signal of a single amplifier while the other respective first end of segments 50 and 60 could be connected in parallel to receive the out-of-phase output signal of the single amplifier, and thus, in this case, driving circuit 70 would only comprise a single amplifier.

Individual segments 50 and 60 are preferably arranged so that respective first ends of any two consecutive segments are substantially adjacent to one another and respective second ends of any two consecutive segments are substantially adjacent to one another. The gap size between any two consecutive segments should be small relative to carder wavelength. For example, about ⅛ in. for a 750 MHz carrier. This arrangement conveniently allows for avoiding time-delay discontinuities between any of the respective individual segments encircling the rotating frame. This allows for effective coupling operation between the transmission line and the coupler at all rotation angles. As shown in FIG. 2, each of the two individual segments 50 and 60 can be designed to subtend a respective angle of about 180° around the circumference of the rotating frame. In general, it will be appreciated that a number of N individual segments each respectively subtending an angle of about 360°/N around the circumference of the rotating frame wherein N is a predetermined even number will be equally effective in alternative embodiments of the present invention since the modulated differential signal (i.e., the net result of the respective modulated signals being substantially 180° out-of-phase with respect to one another) in each case is available for reception anywhere along the circumference of the rotating frame including any gaps between any of the N individual segments. As suggested above, there may be applications which can tolerate a predetermined time delay between the individual segments. In this case, the N number of individual segments need not be limited to an even number since a predetermined odd number of individual segments could be effectively utilized for applications which tolerate such predetermined time delay. The foregoing construction for the individual segments assumes that each segment is made up of a material having a substantially similar dielectric constant. However, it will be apparent that segment materials having predetermined different dielectric constants can also be conveniently employed. In this case, the angle subtended by each respective individual segment need not be identical to each other.

The apparatus of the present invention further comprises a differential coupler 100 attached to stationary frame 12 (FIG. 1) and being positioned in a passage defined by a transmission line shield 150 (FIGS. 4A and 4B) sufficiently near the differentially driven transmission line for establishing radio coupling therebetween in order to receive the modulated differential signal being applied to the respective individual segments. As used herein the expression "radio coupling" refers to noncontactive transfer of energy by electromagnetic radiation at radio frequencies.

It will be appreciated that coupler 100 has a predetermined length dimension along a coupler axis 102 which, for example, can be substantially parallel relative to individual segments 50 and 60. The coupler length dimension is conveniently chosen to be sufficiently short to substantially avoid frequency-dependent directional coupling effects, and to be sufficiently long to avoid substantial signal reduction in coupler 100 whenever the coupler passes about any gap between respective ones of the individual segments. As indicated by arrows 104 and 106, the modulated differential signal applied to respective segments 50 and 60 propagates in opposite directions and thus to avoid blind spots near any of the gaps, coupler 1 00 preferably has a first end 110 directly connected to output port means 112, such as a coaxial line pair or other suitably shielded electrical conductor pair, and has a second end 108 which is substantially free of any termination impedance, i.e., termination resistors. In this manner, the modulated differential signal received by coupler 100 passes to coaxial line pair 112 independently of the propagation direction of the received modulated differential signal, i.e., independently of the propagation direction of the respective electromagnetic waves traveling in individual segments 50 and 60. For instance, waves arriving at second end 108 readily propagate toward the first end and from there to coaxial line pair 112, whereas waves arriving at first end 110 are eventually reflected back from the resistively unterminated second end 108 toward the first end and from there to coaxial line pair 112. In each case, differential coupler 100 advantageously allows for noncontactively extracting the respective 180° out-of-phase signals which constitute the modulated differential signal in the transmission line along the full circumference of the rotating frame. An amplifier 114 can readily provide a predetermined amplification to the respective substantially 180° out-of-phase signals being supplied by differential coupler 100. As will be appreciated by those skilled in the art, the length dimension of the coupler can vary depending on the specific value of the carrier frequency being utilized for the modulated signal. By way of example and not of limitation, the coupler length dimension can be chosen in the range of $\lambda/4$ to $\lambda/8$ wherein $\lambda$ represents the wavelength of the carrier in the transmission line material. Other configurations for the coupler will be readily apparent to those skilled in the art. For example, a relatively short (e.g., about $\lambda/16$) center-tapped coupler can alternatively be employed in lieu of a coupler having a resistively unterminated end.

FIG. 3 illustrates a cross section of a substantially planar transmission line which can be effectively used both for the differentially driven transmission line segments and for the differential coupler. For example, FIG. 3 shows a microstrip 200 wherein substantially parallel first and second signal conductors 202 and 203 and a ground plane 206 are separated from one another by a suitable dielectric material 204. It will be appreciated that such substantially planar transmission line can be readily fabricated employing well known printed circuit techniques which allow for substantial savings in cost as compared to an optical data link. Similarly, a stripline transmission line wherein the first and second signal conductors are "sandwiched" in a respective dielectric material between two ground planes can be alternatively employed both for the transmission line segments and for the coupler. Furthermore, the coupler need not consist of a microstrip or a stripline transmission line. A suitable conductor, such as a short piece of twin wires, aligned substantially parallel to the driven transmission line, will also work effectively.

Figure 4A:
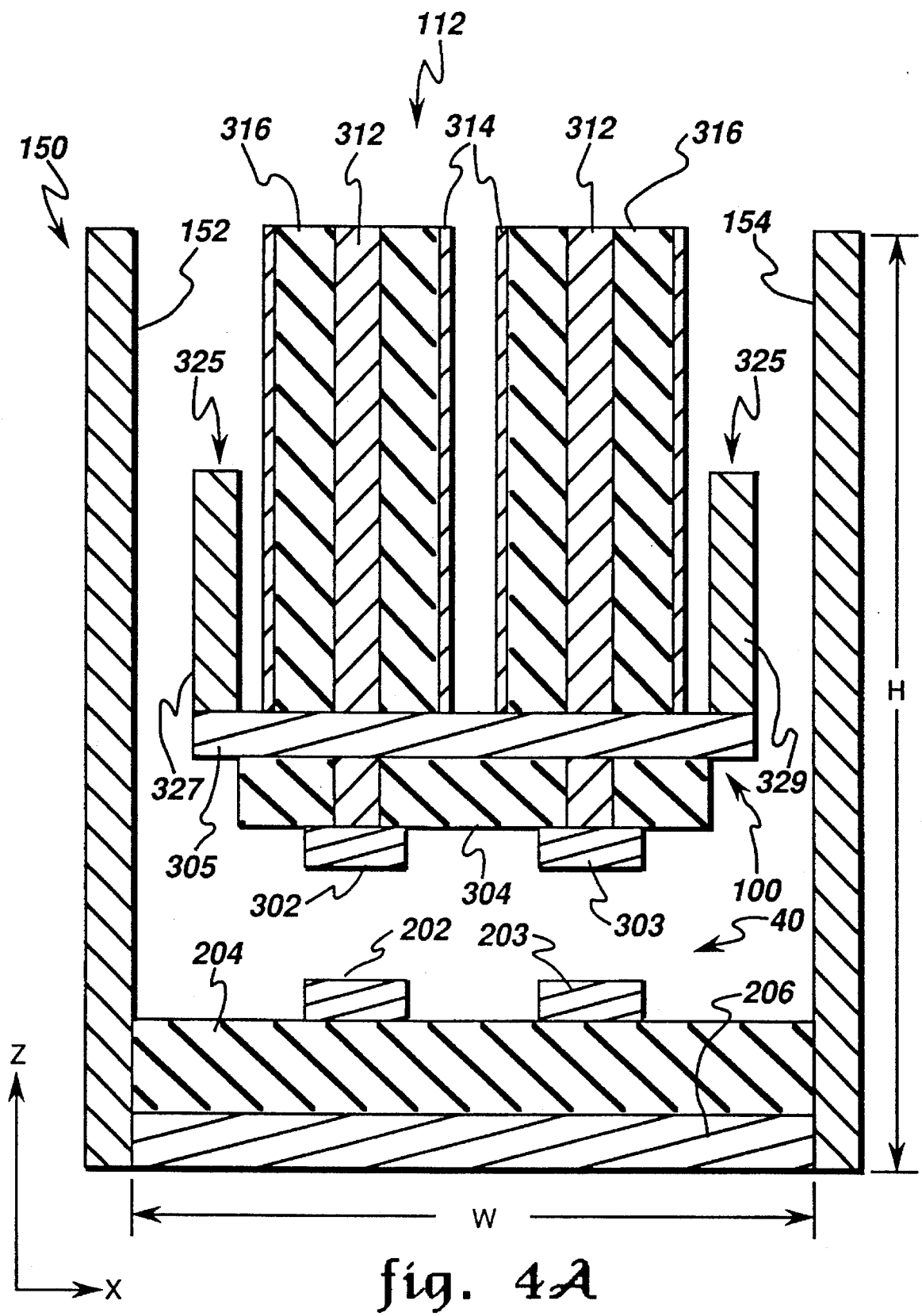
FIGS. 4A and 4B are respective cross sectional views showing the differentially driven transmission line of FIG. 2 and a differential coupler each being respectively shielded in accordance with respective exemplary embodiments of the present invention.
Figure 4B:
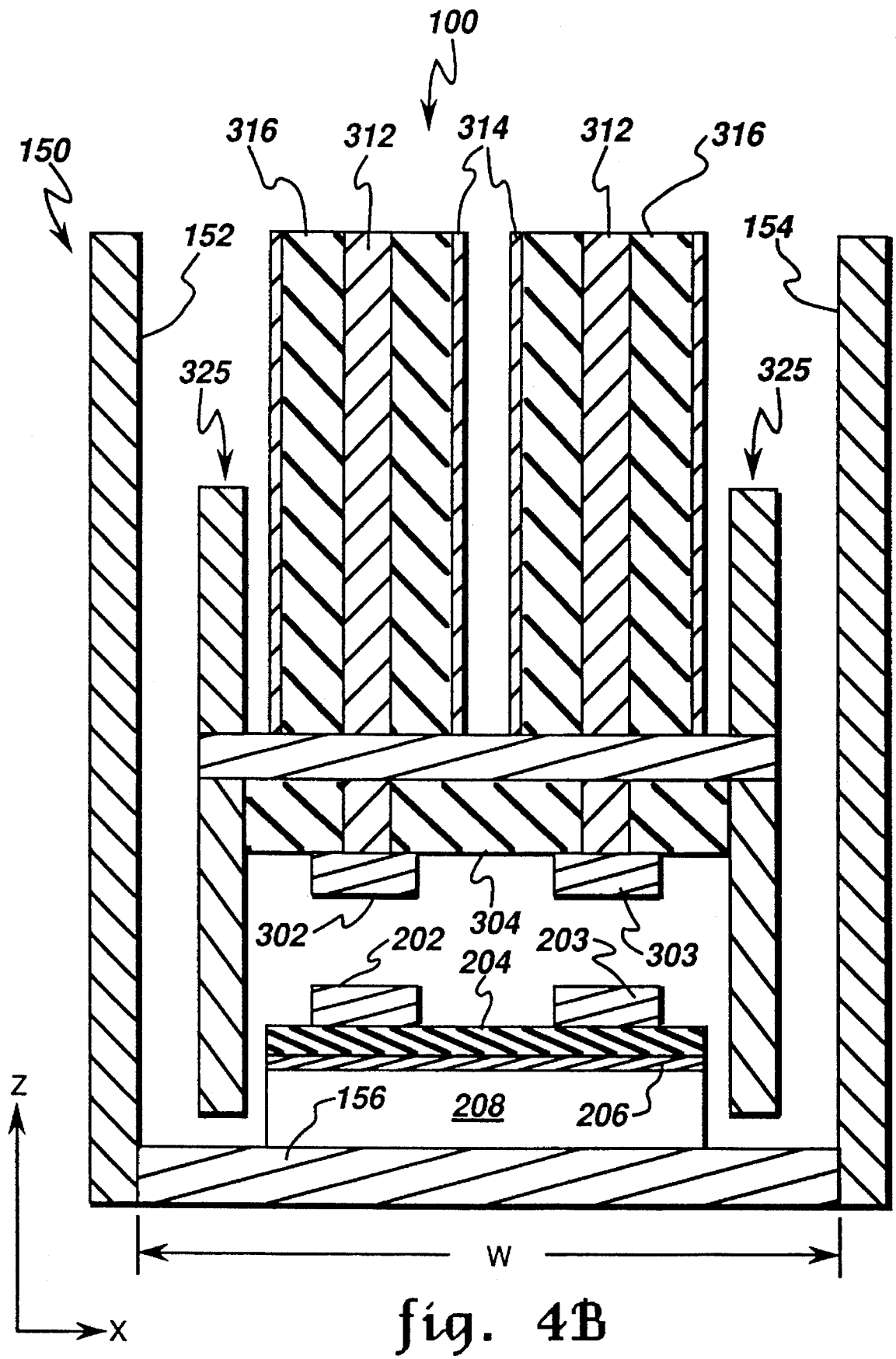

FIG. 4A shows that, as discussed in the context of FIG. 2, transmission line shield means 150 is affixed to transmission line 40 for shielding the transmission line from electromagnetic radiation, i.e., shield means 150 allows for reducing the susceptibility of transmission line 40 to externally produced electromagnetic energy. As seen in FIGS. 4A and 4B, transmission line shield means 150 comprises a U-shaped structure which defines a passage, such as an open passage, around the rotating frame. As seen in FIG. 4A, transmission line shield means 150 can be made-up of a pair of opposite side walls 152 and 154 having a respective end or edge affixed to ground plane 206 of the transmission line segments. In this embodiment, ground plane 206 of the transmission line segments can conveniently provide the bottom wall of the U-shaped structure. The opposite side walls can have a predetermined height H and ground plane 206 can have a predetermined width W. The ratio defined by H/W is suitably chosen so that the U-shaped structure forms a waveguide which is below cutoff for the frequencies of interest. For example, below cutoff, waves having respective transverse magnetic (TM) and transverse electric (TE) propagation modes are evanescent and thus such waves decay rapidly and substantially along the Z axis direction. Electromagnetic waves having a transverse electric and magnetic (TEM) propagation mode can readily propagate in the U-shaped structure, but only if their respective electric fields E are aligned along the X axis direction, i.e., electromagnetic waves having a respective TEM mode and having their respective electric fields aligned other than along the X axis are effectively filtered out from the U-shaped structure. This is because signal conductors 202 and 203 are substantially parallel to the opposite side walls. In particular, waves propagating in the transmission line have respective E fields that are predominantly Z directed. Hence, the U-shaped structure forms a waveguide which is below cutoff for waves having respective TE and TM propagation modes and which is an effective cross-polarization choke or filter for waves having a TEM propagation mode. The electromagnetic amplitude attenuation in the U-shaped structure for waves having a sufficiently long wavelength relative to width W (e.g., $W \leq \lambda/2$), and having respective TE and TM propagation modes can be described by $$A \propto e^{-(\pi/W)^2} \qquad \text{Eq. 1,}$$

wherein z represents a variable along the Z axis direction, and A represents wave amplitude. For example, external waves having respective TE and TM propagation modes are attenuated by 55 dB at the bottom of the U-shaped structure if H/W=2. FIG. 4A further shows a differential coupler 100 having first and second signal conductors 302 and 303 substantially parallel to one another and being positioned to face first and second signal conductors 202 and 203 of the respective separate transmission line segments. The coupler signal conductors are attached to a dielectric material 304 and the respective signals carried by the coupler signal conductors can be readily supplied to amplifier 114 (FIG. 2) via suitable coaxial line pair 112 respectively having an inner conductor 312 in a suitable dielectric material 316 surrounded by an outer shield 314. FIG. 4A also shows an exemplary U-shaped coupler shield 325 for shielding coupler 100 from electromagnetic radiation. As shown in FIG. 4A, the U-shaped coupler shield is made up of a pair of side walls 327 and 329 attached to a ground plane 305 of coupler 100. As shown in FIGS. 4A and 4B, the coupler shield is electrically connected to each outer shield 314 of the coaxial line pair.

FIG. 4B shows that transmission line shield means 150 can be made up of a pair of opposite side walls 152 and 154 having a predetermined height H and a bottom wall 156 having a predetermined width W. Each of the separate transmission line segments is mounted on a suitable substrate 208 which in turn is respectively attached to the bottom wall within opposite side walls 152 and 154. As described in the context of FIG. 4A, the U-shaped structure for the transmission line shield has a ratio defined by H/W chosen to substantially attenuate electromagnetic waves having respective TM and TE propagation modes, wherein H is the height of the opposite side walls 152 and 154 and W is the width of bottom wall 156. FIG. 4B further shows that coupler shield means 325 in this exemplary embodiment is an H-shaped shield which extends sufficiently in the passage defined by the transmission line shield so as to substantially enclose the differentially driven transmission line.

Figure 5:
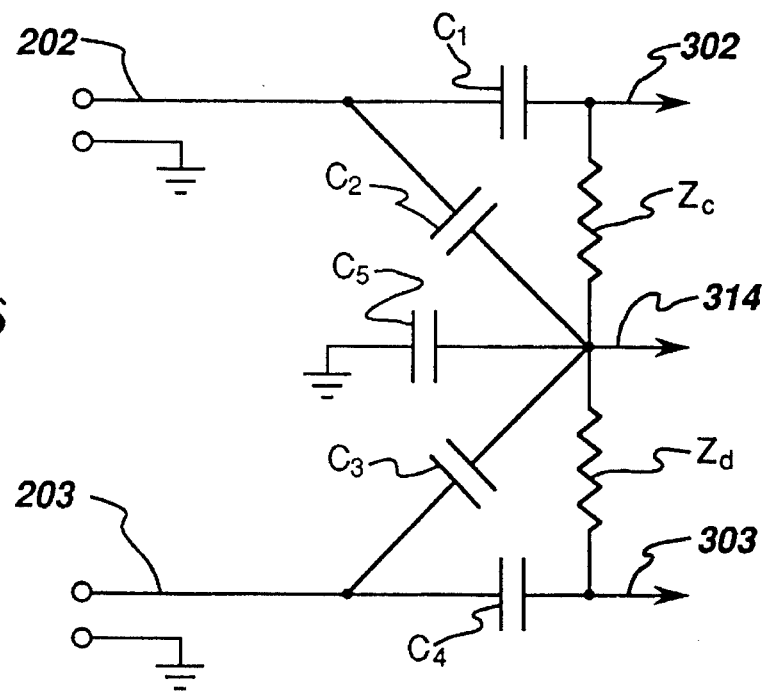
FIG. 5 is a schematic simplified circuit model for the differentially driven transmission line and differential coupler in accordance with the present invention.
Figure 6:
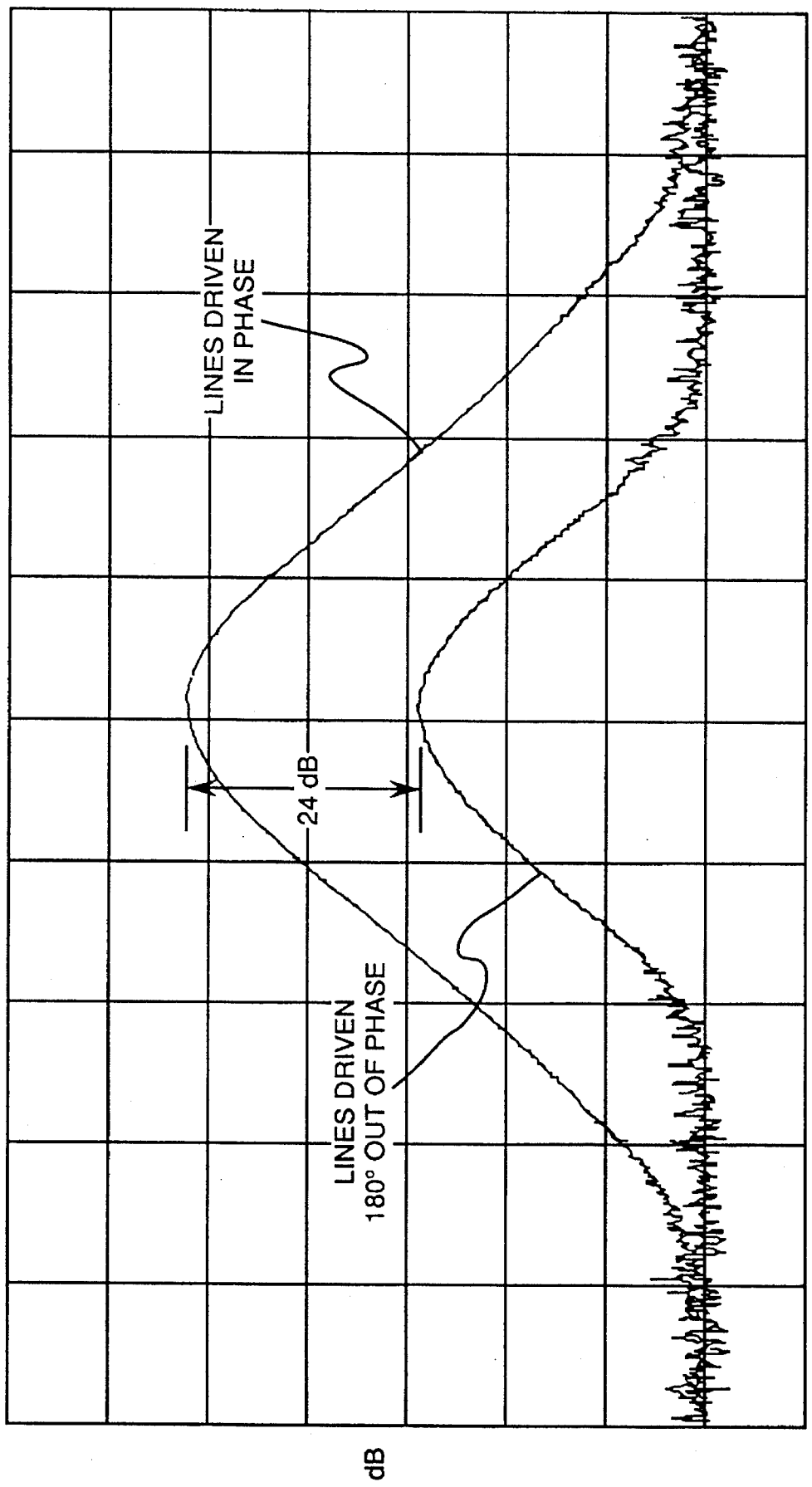
FIG. 6 is a diagram showing respective electromagnetic radiation output characteristics of a differentially driven transmission line in accordance with the present invention and a transmission line not driven differentially.

FIG. 5 shows a simplified equivalent circuit model for the electromagnetic coupling between a differentially driven transmission line and a differential coupler. Capacitors $C_1$–$C_5$ in FIG. 6 represent respective capacitive coupling impedances between transmission line signal conductors 202 and 203 and coupler signal conductor 302 and 303; and between transmission line signal conductors 202 and 203 and outer shield 314 for coaxial line pair 112. The resistors labeled $Z_c$ and $Z_d$ in FIG. 6 represent respective input impedances for the coaxial line pair. As will be appreciated by those skilled in the art, any current which is induced on the respective outer shields of the coaxial line pair will detrimentally affect the operation of the communication link. For example, if such outer shield current is left uncorrected, the operation of the communication link can be degraded due to undesirable electromagnetic radiation around the coupler or due to susceptibility of the coupler to eternally produced electromagnetic energy. In each case, the present invention advantageously allows for minimizing the level of any outer shield current which may cause the above-described degradation to the communication link. Capacitor $C_5$ represents the capacitance between each outer shield 314 and the transmission line ground plane. It can be shown that there will be no current induced in outer shield 314 if $Z_c=Z_d$, $C1=C4$ and $C2=C3$ or, alternatively, if $C5$ were replaced with a short circuit. The capacitance values are essentially determined by the spacing between the coupler and the transmission line and the relative alignment between the coupler signal conductors and the transmission line signal conductors. The input impedances $Z_c$ and $Z_d$ can be made substantially equal to one another by proper termination at the end connected to a suitable signal processor (not shown) for processing the differential signal supplied by the coupler.

Sensitivity to coupler alignment errors can also be conveniently reduced by increasing the value of $C_5$. This may be readily accomplished by providing either of the respective coupler shields discussed in the context of FIGS. 4A and 4B. Sensitivity to roll misalignment of the coupler is conveniently reduced by suitably increasing the spacing between the coupler and the transmission line, while sensitivity to yaw misalignment is reduced by reducing the length of the coupler lines.

FIG. 6 is an exemplary plot showing electromagnetic radiation attenuation characteristics of a differentially driven transmission line (i.e., a transmission line receiving respective signals being substantially 180° out-of-phase with respect to one another) in accordance with the present invention and a transmission line not driven differentially (i.e., a transmission line receiving respective signals being substantially in-phase with respect to one another). In this example, it can be seen that the differentially driven transmission line advantageously provides a 24 dB peak attenuation reduction over the non-differentially driven transmission line.

Although various specific constructions have been given for the present invention, it is to be understood that these are for illustrative purposes only. Various modifications and adaptations will be readily apparent to those skilled in the art without departing from the substance or scope of the invention. For example, although the shielded transmission line segments have been described as rotating along with rotating frame or gantry 15 (FIG. 1) and the coupler has been described as attached to stationary frame 12 (FIG. 1), it is equally possible to instead have the shielded transmission line segments stationary and the coupler mounted on the rotating frame, i.e., stationary and rotating mechanical mounting for the coupler and transmission line segments can be readily interchanged with equally effective results. Accordingly, it is intended that the invention be limited only by the spirit and scope of the claims appended hereto.

What is claimed is:

1. In a computerized tomography system having a stationary frame and a generally annular rotating frame, an apparatus comprising:

a differentially driven transmission line attached to said rotating frame and positioned substantially around said rotating frame, said differentially driven transmission line comprising individual segments each having a respective first end and a respective second end, each of said individual segments having a respective electrical length chosen so that a modulated signal simultaneously applied at each respective first end has a predetermined time-delay upon arrival at each respective second end, said individual segments being arranged so that respective first ends of any two consecutive segments are substantially adjacent to one another and respective second ends of any two consecutive segments are substantially adjacent to one another to avoid time-delay discontinuity in the modulated signal propagating therethrough;

transmission line shield means affixed to said transmission line for shielding said transmission line from electromagnetic radiation, said shield means defining a passage around said rotating frame; and a differential coupler attached to said stationary frame and being positioned in said passage sufficiently near said differentially driven transmission line for establishing radio coupling therebetween so as to receive the modulated signal being applied to the respective individual segments.

2. The apparatus of claim 1 wherein each of said individual segments comprises a respective substantially planar transmission line having first and second signal conductors aligned substantially parallel with respect to one another.

3. The apparatus of claim 2 wherein said differential coupler comprises a substantially planar transmission line having first and second signal conductors aligned substantially parallel with respect to one another and being respectively positioned substantially parallel relative to the first and second signal conductors of the respective individual segments.

4. The apparatus of claim 3 further comprising a coupler shield attached to said differential coupler.

5. The apparatus of claim 4 wherein said coupler shield comprises a U-shaped shield.

6. The apparatus of claim 4 wherein said coupler shield comprises an H-shaped shield extending sufficiently in said passage to substantially enclose the respective individual segments.

7. The apparatus of claim 4 wherein the substantially planar transmission line for said differential coupler comprises a transmission line selected from the group consisting of microstrip and stripline transmission lines.

8. The apparatus of claim 7 further comprising driving means for simultaneously applying at each respective first and second signal conductors of said individual segments respective signals being substantially 180° out-of-phase with respect to one another.

9. The apparatus of claim 8 wherein each respective second end of said individual segments is connected to a predetermined electrical impedance.

10. The apparatus of claim 3 wherein said transmission line shield means comprises a U-shaped structure.

11. The apparatus of claim 10 wherein said U-shaped structure comprises a pair of opposite side walls having a predetermined height H and a bottom wall having a predetermined width W.

12. The apparatus of claim 11 wherein each respective one of said substantially planar transmission lines forming the respective individual segments has its respective first and second signal conductors positioned substantially parallel relative to said pair of opposite walls and has a respective ground plane having a width dimension sufficient to fit within said opposite side walls.

13. The apparatus of claim 12 wherein each of said substantially planar transmission lines forming the respective individual segments comprises a transmission line selected from the group consisting of microstrip and stripline transmission lines.

14. The apparatus of claim 11 wherein each of said individual segments is mounted within said opposite side walls on a substrate attached to said bottom wall.

15. The apparatus of claim 11 wherein the ratio defined by H/W is chosen to substantially attenuate electromagnetic waves having respective transverse magnetic (TM) and transverse electric (TE) propagation modes.

16. The apparatus of claim 10 wherein said U-shaped structure comprises a pair of opposite side walls having a respective end affixed to said individual segments, each of said opposite walls having a predetermined height H.

17. The apparatus of claim 16 wherein each respective one of the substantially planar transmission lines forming the respective individual segments has its respective first and second signal conductors positioned substantially parallel relative to said pair of side walls and has a respective ground plane having a predetermined width W, said ground plane forming a bottom wall attached to said pair of side walls.

18. The apparatus of claim 17 wherein the ratio defined by H/W is chosen to substantially attenuate electromagnetic waves having respective transverse magnetic (TM) and transverse electric (TE) propagation modes.

19. The apparatus of claim 3 wherein said differentially driven transmission line comprises at least two individual segments each respectively subtending a predetermined angle around said rotating frame.

20. The apparatus of claim 19 wherein each respective one of said at least two individual segments subtends an angle of about 180° around said rotating frame.

21. The apparatus of claim 3 wherein said differentially driven transmission line comprises a predetermined number N of individual segments each respectively subtending a predetermined angle around said rotating frame.

22. The apparatus of claim 21 wherein the number N of individual segments is a predetermined even number.

23. The apparatus of claim 21 wherein each respective one of the N individual segments subtends an angle of about 360°/N around said rotating frame.

24. A computerized tomography system comprising:
a stationary frame;
a generally annular rotating frame;
a differentially driven transmission line attached to said rotating frame and positioned substantially around said rotating frame, said differentially driven transmission line comprising individual segments each having a respective first end and a respective second end, each of said individual segments having a respective electrical length chosen so that a modulated signal simultaneously applied at each respective first end has a predetermined time-delay upon arrival at each respective second end, said individual segments being arranged so that respective first ends of any two consecutive segments are substantially adjacent to one another and respective second ends of any two consecutive segments are substantially adjacent to one another to avoid time-delay discontinuity in the modulated signal propagating therethrough;
transmission line shield means affixed to said transmission line for shielding said transmission line from electromagnetic radiation, said shield means defining a passage around said rotating frame; and
a differential coupler attached to said stationary frame and being positioned in said passage sufficiently near said differentially driven transmission line for establishing radio coupling therebetween so as to receive the modulated signal being applied to the respective individual segments.

25. The computerized tomography system of claim 24 wherein each of said individual segments comprises a respective substantially planar transmission line having first and second signal conductors aligned substantially parallel with respect to one another.

26. The computerized tomography system of claim 25 wherein said differential coupler comprises a substantially planar transmission line having first and second signal conductors aligned substantially parallel with respect to one another and being respectively positioned substantially parallel relative to the first and second signal conductors of the respective individual segments.

27. The computerized tomography system of claim 26 further comprising a coupler shield attached to said differential coupler.

28. The computerized tomography system of claim 27 wherein said coupler shield comprises a U-shaped shield.

29. The computerized tomography system of claim 27 wherein said coupler shield comprises an H-shaped shield extending sufficiently in said passage to substantially enclose the respective individual segments.

30. The computerized tomography system of claim 27 wherein the substantially planar transmission line for said differential coupler comprises a transmission line selected from the group consisting of microstrip and stripline transmission lines.

31. The computerized tomography system of claim 30 further comprising driving means for simultaneously applying at each respective first and second signal conductors of said individual segments respective signals being substantially 180° out-of-phase with respect to one another.

32. The computerized tomography system of claim 31 wherein each respective second end of said individual segments is connected to a predetermined electrical impedance.

33. The computerized tomography system of claim 26 wherein said transmission line shield means comprises a U-shaped structure.

34. The computerized tomography system of claim 33 wherein said U-shaped structure comprises a pair of opposite side walls having a predetermined height H and a bottom wall having a predetermined width W.

35. The computerized tomography system of claim 34 wherein each respective one of said substantially planar transmission lines forming the respective individual segments has its respective first and second signal conductors positioned substantially parallel relative to said pair of opposite walls and has a respective ground plane having a width dimension sufficient to fit within said opposite side walls.

36. The computerized tomography system of claim 35 wherein each of said substantially planar transmission lines forming the respective individual segments comprises a transmission line selected from the group consisting of microstrip and stripline transmission lines.

37. The computerized tomography system of claim 34 wherein each of said individual segments is mounted within said opposite side walls on a substrate attached to said bottom wall.

38. The computerized tomography system of claim 34 wherein the ratio defined by H/W is chosen to substantially attenuate electromagnetic waves having respective transverse magnetic (TM) and transverse electric (TE) propagation modes.

39. The computerized tomography system of claim 33 wherein said U-shaped structure comprises a pair of opposite side walls having a respective end affixed to said individual segments, each of said opposite walls having a predetermined height H.

40. The computerized tomography system of claim 39 wherein each respective one of the substantially planar transmission lines forming the respective individual segments has its respective first and second signal conductors positioned substantially parallel relative to said pair of side walls and has a respective ground plane having a predetermined width W, said ground plane forming a bottom wall attached to said pair of side walls.

41. The computerized tomography system of claim 40 wherein the ratio defined by H/W is chosen to substantially attenuate electromagnetic waves having respective transverse magnetic (TM) and transverse electric (TE) propagation modes.

42. The computerized tomography system of claim 26 wherein said differentially driven transmission line comprises at least two individual segments each respectively subtending a predetermined angle around said rotating frame.

43. The computerized tomography system of claim 42 wherein each respective one of said at least two individual segments subtends an angle of about 180° around said rotating frame.

44. The computerized tomography system of claim 26 wherein said differentially driven transmission line comprises a number N of individual segments each respectively subtending a predetermined angle around said rotating frame wherein N is a predetermined even number.

45. The computerized tomography system of claim 44 wherein the number N of individual segments is a predetermined even number.

46. The computerized tomography system of claim 44 wherein each respective one of the N individual segments subtends an angle of about 360°/N around the rotating frame.

* * * * *